United States Patent
Grant et al.

(10) Patent No.: US 12,007,392 B2
(45) Date of Patent: Jun. 11, 2024

(54) METHOD AND SYSTEM FOR DETECTION OF MYCOBACTERIA IN HUMAN SAMPLES

(71) Applicants: Temple University—Of The Commonwealth System of Higher Education, Philadelphia, PA (US); Queen's University Belfast, Belfast (GB); St. George's, University of London, Tooting (GB); University of Central Florida, Orlando, FL (US)

(72) Inventors: Irene Grant, Belfast (GB); Antonio Foddai, Abbington, PA (US); John Todd Kuenstner, Abbington, PA (US); Raghava Potula, Philadelphia, PA (US); Tim Bull, Tooting (GB); Saleh Naser, Orlando, FL (US); Ira Shafran, Winter Park, FL (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 16/585,391

(22) Filed: Sep. 27, 2019

(65) Prior Publication Data
US 2020/0103403 A1 Apr. 2, 2020

Related U.S. Application Data

(60) Provisional application No. 62/737,609, filed on Sep. 27, 2018.

(51) Int. Cl.
*G01N 33/569* (2006.01)

(52) U.S. Cl.
CPC ... *G01N 33/5695* (2013.01); *G01N 2800/065* (2013.01); *G01N 2800/56* (2013.01)

(58) Field of Classification Search
None
See application file for complete search history.

(56) References Cited

PUBLICATIONS

Swift, PhD Thesis, 2014, University of Nottingham, "Development of rapid phage based detection methods for mycobacteria". (Year: 2014).*
Naser et al., The Lancet, 2004, 364:1039-1044. (Year: 2004).*
Patterson et al., medRxiv preprint, Sep. 27, 2021 (https://doi.org/10.1101/2021.09.27.21263960). (Year: 2021).*
Bach et al., Journal of Crohn's and Colitis, 2012, 6, 628-629. (Year: 2012).*
Chamberlin et al., Aliment Pharmacol Ther, 2001, 15: 337-346. (Year: 2001).*
Abubakar I, Myhill D, Aliyu SH, Hunter PR. Detection of *Mycobacterium avium* subspecies paratuberculosis from patients with Crohn's disease using nucleic acid-based techniques: a systematic review and meta-analysis. Inflamm Bowel Dis. Mar. 2008;14(3):401-10.
Bull TJ, Munshi T, Mikkelsen H, Hartmann SB, Sørensen MR, Garcia JS, Lopez-Perez PM, Hofmann S, Hilpert K, Jungersen G. Improved Culture Medium (TiKa) for *Mycobacterium avium* Subspecies Paratuberculosis (MAP) Matches qPCR Sensitivity and Reveals Significant Proportions of Non-viable MAP in Lymphoid Tissue of Vaccinated MAP Challenged Animals. Front Microbiol. Jan. 4, 2017;7:2112.
Ellingson JL, Anderson JL, Koziczkowski JJ, Radcliff RP, Sloan SJ, Allen SE, Sullivan NM. Detection of viable *Mycobacterium avium* subsp. paratuberculosis in retail pasteurized whole milk by two culture methods and PCR. J Food Prot. May 2005;68(5):966-72.
Feller M, Huwiler K, Stephan R, Altpeter E, Shang A, Furrer H, Pfyffer GE, Jemmi T, Baumgartner A, Egger M. *Mycobacterium avium* subspecies paratuberculosis and Crohn's disease: a systematic review and meta-analysis. Lancet Infect Dis. Sep. 2007;7(9):607-13.
Grant IR, Ball HJ, Rowe MT. Incidence of *Mycobacterium paratuberculosis* in bulk raw and commercially pasteurized cows' milk from approved dairy processing establishments in the United Kingdom. Appl Environ Microbiol. May 2002;68(5):2428-35.
Grant IR, Foddai ACG, Tarrant JC, Kunkel B, Hartmann FA, McGuirk S, Hansen C, Talaat AM, Collins MT. Viable *Mycobacterium avium* ssp. paratuberculosis isolated from calf milk replacer. J Dairy Sci. Dec. 2017;100(12):9723-9735.
Lichtenstein GR, Loftus EV, Isaacs KL, Regueiro MD, Gerson LB, Sands BE. ACG Clinical Guideline: Management of Crohn's Disease in Adults. Am J Gastroenterol. Apr. 2018;113(4):481-517.
Magombedze G, Ngonghala CN, Lanzas C. Evaluation [corrected] of the "Iceberg Phenomenon" in Johne's disease through mathematical modelling. PLoS One. Oct. 22, 2013;8(10):e76636.
McClure HM, Chiodini RJ, Anderson DC, Swenson RB, Thayer WR, Coutu JA. *Mycobacterium paratuberculosis* infection in a colony of stumptail macaques (*Macaca arctoides*). J Infect Dis. May 1987;155(5):1011-9.
Naser SA, Schwartz D, Shafran I. Isolation of *Mycobacterium avium* subsp paratuberculosis from breast milk of Crohn's disease patients. Am J Gastroenterol. Apr. 2000;95(4):1094-5.
National Research Council (US) Committee on Diagnosis and Control of Johne's Disease. Diagnosis and Control of Johne's Disease. Washington (DC): National Academies Press (US); 2003.
St-Jean G, Jernigan AD. Treatment of *Mycobacterium paratuberculosis* infection in ruminants. Vet Clin North Am Food Anim Pract. Nov. 1991;7(3):793-804.
Zhang et al., "Cross-reactivity of antibodies against microbial proteins to human tissues as basis of Crohn's disease and Sjogren's syndrome," 2017, bioRxiv: doi.org/10.1101/116574.
Swift, Benjamin MC, "Development of rapid phage based detection methods for mycobacteria." PhD thesis, University of Nottingham (2014); http://eprints.nottingham.ac.uk/14225/1/FINAL_whole_Thesis.pdf, 349 pages.†

(Continued)

*Primary Examiner* — Nicole Kinsey White
(74) *Attorney, Agent, or Firm* — Riverside Law LLP

(57) ABSTRACT

The present invention provides a semi-quantitative phage-based assay for Mycobacterial infection, in which the phage assay plaque count correlates to the number of viable Mycobacterial organisms in the subject sample, and methods of use thereof for diagnosing, treating or monitoring Mycobacterial infection.

10 Claims, 3 Drawing Sheets

(56) References Cited

PUBLICATIONS

Gerrard, Zara E., et al. "Survival of *Mycobacterium avium* subspecies paratuberculosis in retail pasteurised milk." Food Microbiology 74 (2018): 57-63.†

Swift, Benjamin MC, et al. "Factors affecting phage D29 infection: a tool to investigate different growth states of mycobacteria." PLoS One 9.9 (2014): e106690, pp. 1-7.†

FASTPlaqueTBTM Assay Kit, Biotec Laboratories, Ltd., version Sep. 11, 2004, pp. 1-19.†

Stanley, Emma C., et al. "Development of a new, combined rapid method using phage and PCR for detection and identification of viable *Mycobacterium paratuberculosis* bacteria within 48 hours." Applied and Environmental Microbiology 73.6 (2007): 1851-1857.†

Swift, Benjamin MC, et al. "Evidence of *Mycobacterium tuberculosis* complex bacteraemia in intradermal skin test positive cattle detected using phage-RPA." Virulence 7.7 (2016): 779-788.†

Swift, Benjamin MC, et al. "Development of a rapid phage-based method for the detection of viable *Mycobacterium avium* subsp. paratuberculosis in blood within 48h." Journal of Microbiological Methods 94.3 (2013): 175-179.†

\* cited by examiner
† cited by third party

METHOD AND SYSTEM FOR DETECTION OF MYCOBACTERIA IN HUMAN SAMPLES

CROSS REFERENCE TO RELATED APPLICATIONS

This application claims priority to U.S. Provisional Application No. 62/737,609, filed Sep. 27, 2018 which is hereby incorporated by reference herein in its entirety.

BACKGROUND OF THE INVENTION

*Mycobacterium avium* subspecies *paratuberculosis* (MAP) has long been suspected to cause Crohn's disease (CD) in humans and is accepted as the cause of Johne's disease (JD), which is a chronic, diarrheal wasting disease of cattle and a wasting disease in sheep and goats (Committee On Diagnosis and Control of Johne's Disease, National Research Council. Diagnosis and Control of Johne's Disease. The National Academies Press. 2003. Washington D.C.). Once an animal is infected, the MAP bacterium grows and multiplies inside the cells of the immune system. The organism is excreted in the feces, and to a lesser extent in milk. Outside the host animal, the bacterium multiplies poorly, but can survive over a year in the environment because of its resistance to heat, cold and the effect of drying. This slow-growing bacterium affects the ileum and causes diarrhea and cachexia. There is no known curative treatment for JD, although there are anecdotal reports of long-term disease suppression using antibiotics (Committee On Diagnosis and Control of Johne's Disease, National Research Council. Diagnosis and Control of Johne's Disease. The National Academies Press. 2003. Washington D.C.; St-Jean G et al., 1991, Vet. Clin. North Am. Food Anim. Pract., 7:793-804). A diarrheal/wasting illness associated with infection with MAP has also been reported in non-human primates (McClure H M et al., 1987, J. Infec. Dis., 155:1011-1019).

A significantly higher percentage of patients with CD as compared to controls have evidence of infection by MAP (Feller M et al., 2007, Lancet. Infect. Dis., 7:607-613; Abubakar I et al., 2008, Inflamm. Bowel Dis., 14:401-410). Furthermore, MAP has been cultured from the blood of CD patients in a significantly greater proportion than in controls (Naser S A et al., 2004, Lancet, 364:1039-1044; Naser S A et al., 2009, Open Inf. J., 2:22-23). The viable MAP bacterium is found in commercially available pasteurized milk (Grant I R et al., 2002, App. Env. Microbiol., 68:2428-2435; Ellingson J L et al., 2005, J. Food Prot., 68:966-972). In fact, 2.7% of retail pasteurized milk samples purchased in Wisconsin, Minnesota and California contained viable MAP (Ellingson et al., 2005, J Food Prot, 68:966-972). Because of the prevalence of this organism in the food chain and because JD is a worldwide zoonosis, it is not surprising that the first mass screening of the human population in a study done in North India on a total of 23,196 serum samples submitted for multiple medical conditions, including diabetes, liver disorders, anemia, thyroid disorders, abdominal disorders, and inflammatory illness, showed that 34% of the samples had evidence of MAP infection by an ELISA antibody test. The same study showed that 12.7% of apparently normal individuals had IS900 PCR evidence of MAP in their blood (Singh S V et al., 2014, J. Public Health and Epidemiology, 6:20-29). However, the current blood culture method for MAP requires 3 to 6 months of growth to recover the organism and is of relatively low reproducibility (Kuenstner J T et al., 2017, Front. Public Health, doi: 10.3389/fpubh.2017.00208).

Thus, there is a need in the art for reproducible, reliable, and fast methods to identify Mycobacterial infections. The present invention satisfies this unmet need.

SUMMARY OF THE INVENTION

In one embodiment, the invention relates to a semiquantitative method for detecting viable target mycobacterial cell in a sample comprising the steps of: a) obtaining a sample from a subject; b) lysing cells of the sample to release any viable target mycobacterial cell; c) admixing a bacteriophage with a sample under conditions suitable to allow the bacteriophage to infect any viable target mycobacterial cell present in the sample; d) removing any bacteriophage not infecting a viable target mycobacterial cell; e) admixing at least a portion of the admixture of step c) following the removal of step d) with bacteria capable of supporting replication of the bacteriophage; f) plating at least a portion of the admixture of step e) on a substrate to support growth of the bacteria; and g) quantifying the number of bacteriophage plaques that form.

In one embodiment, the sample is human blood, body fluid or tissue. In one embodiment, the sample comprises peripheral blood mononuclear cells (PBMC).

In one embodiment, the subject has been diagnosed with Crohn's disease.

In one embodiment, the cells are lysed by osmotic shock.

In one embodiment, the sample from a human suspected of being infected with the target mycobacterial cell. In one embodiment, the target mycobacterial cell is *Mycobacterium avium* subspecies *paratuberculosis* (MAP), *Mycobacterium avium* complex (MAC), *Mycobacterium avium* hominissuis (MAH), *Mycobacterium tuberculosis* (MTB), *Mycobacterium leprae*, *Mycobacterium vaccae*, *Mycobacterium celatum*, *Mycobacterium kansasii*, *Mycobacterium gordonae*, *Mycobacterium porcinum*, *Mycobacterium cheloni*, *Mycobacterium flavescens*, *Mycobacterium bovis*, *Mycobacterium sylvaticum* or *Mycobacterium bovis* Bacillus Calmette Guerin (BCG).

In one embodiment, the bacteriophage is a broad host range mycobacteriophage, D29 or TM4.

In one embodiment, the DNA is analyzed by whole genome sequencing or a PCR based DNA amplification system. In one embodiment, the DNA is analyzed by PCR using primers that anneal specifically to a signature DNA sequence that occurs in the target mycobacterial cell. In one embodiment, the signature DNA sequence is IS900, IS1245, f57 or IS6110.

In one embodiment, the method further comprises discriminating between diseased and asymptomatic subjects, comprising identifying the subject as diseased when the number of bacteriophage plaques is statistically significantly greater than a reference number of bacteriophage plaques, or as asymptomatic when the number of bacteriophage plaques is not statistically significantly greater than a reference number of bacteriophage plaques. In one embodiment, the subject is a human host and wherein the reference number of bacteriophage plaques is a reference number of plaques in asymptomatic human hosts.

In one embodiment, the method further comprises a step of assessing Crohn's disease (CD) severity.

In one embodiment, the method further comprises a step of identifying latent paratuberculosis in humans.

In one embodiment, the method further comprises a step of using the plaque count numbers as a guide to therapy in humans and to correlate treatment outcomes.

In one embodiment, the method is used as a guide to therapy for a disease associated with infection with at least one selected from the group consisting of MAP, MAC, MAH, MTB, *Mycobacterium leprae*, *Mycobacterium bovis*, *Mycobacterium sylvaticum* and BCG.

In one embodiment, the invention relates to a kit for detecting viable target mycobacterial cell in a sample comprising D29 bacteriophage and at least one nucleic acid probe. In one embodiment, the probe is selected from the group consisting of IS900, IS1245, f57 and IS6110.

BRIEF DESCRIPTION OF THE DRAWINGS

The following detailed description of various embodiments of the invention will be better understood when read in conjunction with the appended drawings. For the purpose of illustrating the invention, there are shown in the drawings illustrative embodiments. It should be understood, however, that the invention is not limited to the precise arrangements and instrumentalities of the embodiments shown in the drawings.

DETAILED DESCRIPTION

Figure 1:
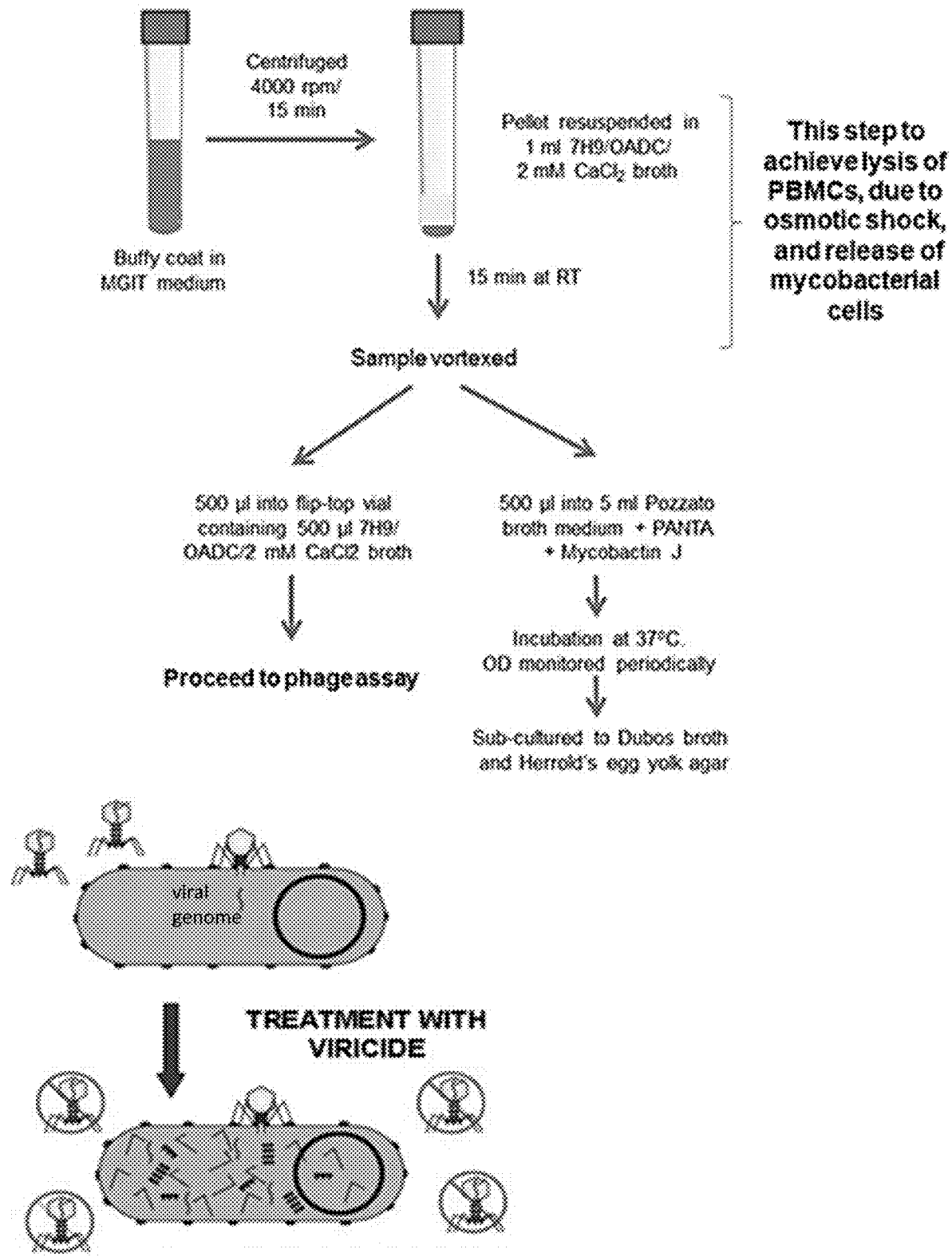
FIG. 1 depicts a schematic diagram of the phage assay as applied to human peripheral blood mononuclear cell (PBMC) samples.
Figure 1:
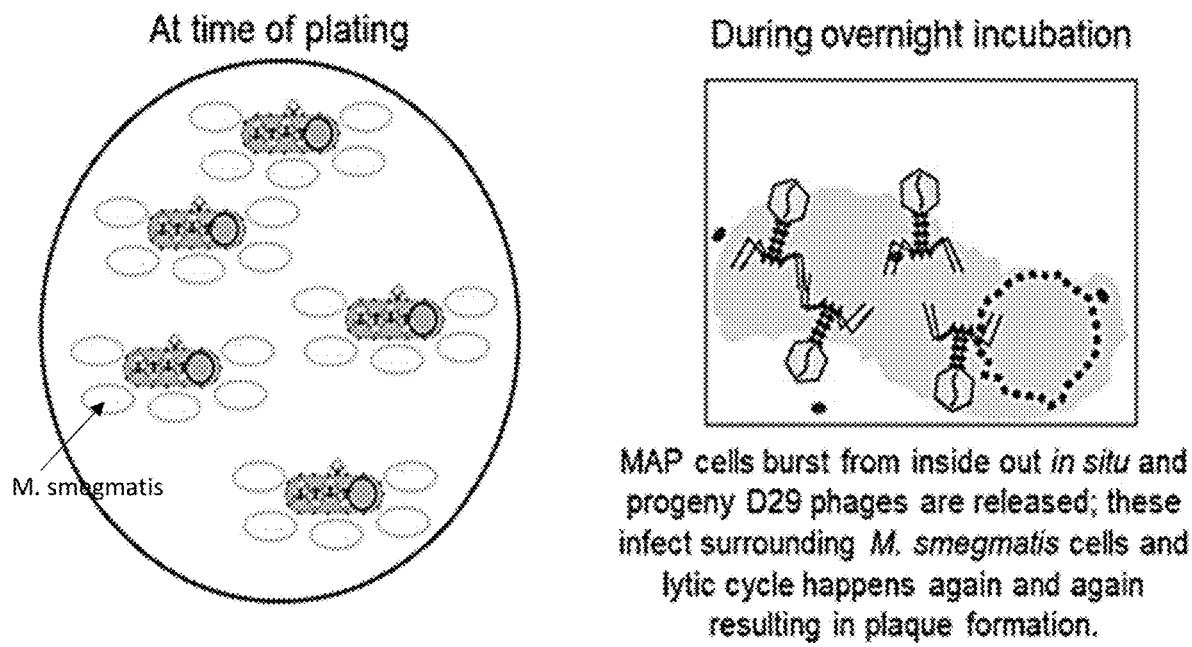
Figure 1:
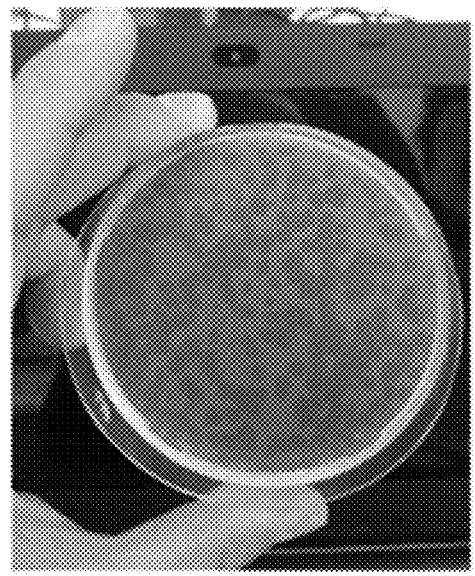

The present invention is based, in part, on the development of a semi-quantitative phage-based assay for Mycobacterial infection, in which the phage assay plaque count correlates to the number of viable Mycobacterial organisms in the subject sample. In one embodiment, the invention provides a method for detection of viable Mycobacterial organisms in human blood. In one embodiment, the invention provides a method for discriminating between diseased and asymptomatic human hosts who are infected by Mycobacteria. In one embodiment, the invention provides a method for assessing Crohn's disease (CD) severity. In one embodiment, the invention provides a method for identifying latent paratuberculosis in humans. In one embodiment, the invention provides a method for guiding Mycobacterial therapy in humans and correlating treatment outcomes with the phage plaque count.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody" as used herein, refers to an immunoglobulin molecule, which is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1988; Houston et al., 1988; Bird et al., 1988).

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease, or disorder, the frequency with which such a sign or symptom is experienced by a patient, or both, is reduced.

"Measuring" or "measurement," or alternatively "detecting" or "detection," means assessing the presence, absence, quantity or amount (which can be an effective amount) of a given substance.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al, Mol. Cell. Probes 8:91-98 (1994)). The term nucleic acid is used interchangeably with gene, cDNA, and mRNA encoded by a gene.

As used herein, the term "subject" refers to a host organism, for example, a human or another animal (e.g., primate, dog, cat, goat, horse, cow, pig, mouse, rat, rabbit, avian and the like.). In many embodiments of the present invention, the subject is a human being. In such embodiments, the subject may be referred to as an "individual" or a "patient."

"Sample" or "biological sample" as used herein means a biological material isolated from an individual, including but is not limited to organ, tissue, exosome, breast milk, blood, plasma, saliva, urine and other body fluid. The biological sample may contain any biological material suitable for detecting the desired biomarkers, and may comprise cellular and/or non-cellular material obtained from the individual.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

The term "microarray" refers broadly to both "DNA microarrays" and "DNA chip(s)," and encompasses all art-recognized solid supports, and all art-recognized methods for affixing nucleic acid molecules thereto or for synthesis of nucleic acids thereon.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention is based in part on the development of an assay which allowed for the demonstration of MAP in human blood and further allows for recovery of organisms in a low bacterial burden human infection. The invention provides a system for detecting a target bacterium in a sample. The present invention provides, in part, a rapid detection method for viable bacterial species in human blood.

The test uses a bacteriophage that attacks the viable bacterial cells, which are released from human white blood cells (WBCs). The viable organisms released from the lysed WBCs are inoculated onto a medium containing cells from a bacterial species that supports bacteriophage growth. The infected cells burst and the phages infect surrounding cells, leaving a zone of clearing called a plaque. The DNA from the center of the plaque contains the DNA from the bacterial cell that infected the patient.

Accordingly, the invention features a method for detecting a target bacterium in a sample. This method includes the steps of: (a) contacting the sample with a bacteriophage that is capable of infecting a target bacterium; (b) removing any excess bacteriophage that did not infect a target bacterium; (c) contacting at least a portion of the purified, infected target bacteria with at least one bacterium that supports growth of the bacteriophage; (d) plating at least a portion of the sample of (c) on a substrate that promotes growth of the at least one bacterium; (e) placing the plate under conditions that promote bacteriophage infection and lysis of the bacterium that supports growth of the bacteriophage and (f) detecting plaque formation. In one embodiment, the method further comprises isolating genomic DNA from the plaque(s) and determining the species or strain of the target bacterium.

Target Bacterium

In one embodiment of the invention, the target bacterium can be a pathogen. In one embodiment the target bacterium is a *mycobacterium*. Exemplary *mycobacterium* that can be detected according to the methods of the invention include, but are not limited to, *Mycobacterium avium* subspecies *paratuberculosis* (MAP), *Mycobacterium avium* complex (MAC), *Mycobacterium avium* hominissuis (MAH), *Mycobacterium tuberculosis* (MTB), *Mycobacterium leprae*, *Mycobacterium vaccae*, *Mycobacterium celatum*, *Mycobacterium kansasii*, *Mycobacterium gordonae*, *Mycobacterium porcinum*, *Mycobacterium cheloni*, *Mycobacterium flavescens*, *Mycobacterium bovis*, *Mycobacterium scrofulaceum*, *Mycobacterium ulcerans*, *Mycobacterium sylvaticum*, *Mycobacterium smegmatis* and *Mycobacterium bovis Bacillus* Calmette Guerin (BCG).

Sample

The sample may be a sample from an animal or human suspected of being infected with the target *mycobacterium*.

The sample from the subject may be any appropriate sample, depending on the suspected infection. In one embodiment, the sample may be bodily fluid, sputum, pus, milk, cerebrospinal fluid, mucosa, skin, blood, urine, tissue and/or faeces. In one embodiment the sample is a sample of blood. The sample may be a sample of a product for human or animal consumption. For example, the sample may be a sample of milk, cheese or a dairy product containing raw milk. Methods for obtaining such samples are well known in the art.

In one embodiment, the test sample may be an aliquot or dilution of the original sample. In one embodiment, the test sample may be a concentration of the original sample.

In one embodiment, eukaryotic cells in the sample are lysed to release microbial cells. Methods of lysing cells are well known in the art. In one embodiment, PBMCs are lysed using osmotic shock. In one embodiment, the PBMCs are lysed by suspending the PBMCs in a medium comprising 7H9, supplemented with 10% Oleic Albumin Dextrose Catalase (OADC) and 2 mM $CaCl_2$. In one embodiment, the PBMCs are incubated at room temperature for at least 5, at least 10, at least 15 or more than 15 minutes to ensure complete lysis of the PBMC and release of mycobacterial cells.

Bacteriophage

The bacteriophage may be any lytic bacteriophage that is able to infect and lyse the target bacteria. The assay can be modified to identify plaques from a variety of bacteriophage using a variety of host bacteria. For example, there are six major families of bacteriophages including Myoviridae (T-even bacteriophages), Styloviridae (Lambda bacteriophage groups), Podoviridae (T-7 and related bacteriophage), Microviridae (X174 group), Leviviridae (for example, *E. coli* bacteriophage MS2) and Inoviridae as well as coliphages, in general, that can be detected using the methods of this invention. Other bacteriophage families include members of the Cystoviridae, Microviridae, and Siphoviridae families. A variety of bacteriophage that form plaques on *E. coli* are known. Bacteriophage that form plaques on *Staphylococcus* are known and these are listed in J. E. Blair and R. E. O. Williams. 1961. "Phage typing of Staphylococci" Bull. W. H. O. 24:771-784; that form plaques in

*Salmonella* including bacteriophage SD11 and SD12 are provided by Stubbs, et al. 1994. J. Clin. Microbiol. 32:199 and Gershman M. 1977. J. Clin. Microbiol. 5:302-314; bacteriophage that form plaques on *Listeria* are known and are provided for example by Van der Mee et al., 1995. Appl. Environ. Microbiol. 61:303; and bacteriophage that form plaques in *Yersinia* include K27 and are provided by Baker et al. 1982. J. Clin. Microbiol. 15:491-502. Bacteriophage of *Pseudomonas* include φ6 (available from the American Type Culture Collection (ATCC), Rockville, Md.), bacteriophage of *Salmonella cholerae* include P22 (available from ATCC), and bacteriophage from *Enterococcus faecalis* includes VD13 (also available from ATCC). In addition bacteriophage capable of replicating in *mycobacterium* species are known as well. In one embodiment, the bacteriophage may be specific to target mycobacteria. The bacteriophage may be any broad host range mycobacteriophage that is able to infect and lyse the target Mycobacteria. For example, the bacteriophage may be D29 or TM4 bacteriophage.

In these assays, a sample comprising a test sample suspected of containing a particular type of bacteria is contacted with bacteriophage. Following an incubation period to permit adsorption of the bacteriophage to the bacteria, bacteriophage not in contact or not infecting the bacteria are removed. There are a number of methods to remove or separate free bacteriophage from bacteria at this stage. A method known in the art is to apply the sample to a centrifuge tube to either separate the bacteria by spinning the bacteria to the bottom of the tube or by separating the bacteria on a cushioning agent such as cellulose, other sugar solutions or other centrifuge density separation compounds known in the art. The method may comprise the use of antibodies, for example antibodies may be used as a capture agent to bind unlysed cells. The method may comprise the use of antibodies as a capture agent to bind unlysed cells but not for identifying Mycobacteria or mycobacterial infection. In one embodiment, the free bacteriophage are removed using a chemical treatment, for example, treatment with ferrous ammonium sulphate (FAS).

Substrates

Substrates for use in the method of the invention include, but are not limited to, to an agar, guar, methylcellulose or other solid or semi-solid gel-type support that permits the formation of a bacterial lawn and permits the visualization of virus plaques. In one embodiment, the support can be formed by hydrating a water hydratable material that can then gel, where the water hydratable material is positioned on a water-proof surface. Alternatively the support can be obtained as a combination of a water-proof support and a solidifiable material applied in liquid form to the water-proof surface.

In one embodiment, the support is an agar-coated petri-plate. Petri-plate agar-based bacteriophage assays are well known. Petri-plates in a variety of sizes, including multi-well culture plates, are well known in the art and available from suppliers such as Fisher Scientific (Pittsburgh, Pa.) and Nunc Nalgene (Rochester, N.Y.). In these assays, agar-containing petri-plates receive a top agar mixture that includes top agar, bacteria capable of supporting replication of a bacteriophage, and at least a portion of a test sample containing the bacteria infected by the bacteriophage. As the bacteriophage replicate, the bacteria lyse, forming plaques or areas of clearing or reduced turbidity on the confluent lawn of bacteria.

Any agar that promotes the growth of bacteriophage-susceptible bacteria can be used. In one embodiment, the agar comprises Bacto-Agar top agar (Becton & Dickinson Microbiology Systems, Cockeysville, Md.) containing nutrient broth (Becton & Dickinson Microbiology Systems) at a pH of about 7.2 to about 7.4. In one embodiment, the agar comprises 7H9 agar supplemented with OADC. Other agar formulations and other solidifying agents can be used in this invention as well. In one embodiment, the top agar is dispensed as a liquid into test tubes.

In one embodiment, a sample of bacteriophage-susceptible bacteria and a sample containing a bacteria infected by a bacteriophage is added to liquid top agar. The mixture is agitated gently and the sample is poured onto an agar plate containing a base agar. The plates are incubated for a time and at a temperature to permit the bacterial lawn to form and for bacteriophage to replicate.

In one embodiment, the bacteriophage-susceptible bacteria is *Mycobacterium smegmatis*.

Following growth and plaque formation, the number of plaques is counted and the amount of bacteriophage is determined based on the dilution of the sample. For example, plaques are counted and the number of plaques is corrected for sample dilution to produce the number of plaques that would be present in a given volume of undiluted sample. Each plaque represents one infectious bacteriophage in the original inoculum; thus, the number of plaques corrected for dilution relates to the number of plaque forming units per volume.

Analysis of Mycobacterial Species

In one embodiment, the assay includes a method of identifying the species or strain of the target mycobacterial cell. In one embodiment, nucleic acid from the lysed *mycobacterium* on the phage assay plate may be isolated and analyzed by any suitable technique to identify the species or strain of the target mycobacterial cell. In one embodiment, nucleic acid from a *mycobacterium* isolated from a sample of a subject identified as having a Mycobacterial infection by the phage assay plate may be isolated and analyzed by any suitable technique to identify the species or strain of the target mycobacterial cell.

Exemplary methods for analysis of nucleic acids include, but are not limited to, amplification techniques, such as PCR and RT-PCR (including quantitative variants), and hybridization techniques, such as in situ hybridization, microarrays, and blots.

In one embodiment, the nucleic acid may be analyzed to identify signature sequences from at least one target Mycobacteria, for example from one or two different target Mycobacteria, or three different target Mycobacteria, or four different target Mycobacteria, or five different target Mycobacteria, or six different target Mycobacteria, or seven different target Mycobacteria, or eight different target Mycobacteria, or nine different target Mycobacteria, or ten different target Mycobacteria or more. The nucleic acid may be analyzed by PCR using primers that anneal, allow amplification, specifically to a signature nucleic acid sequence that occurs in the target Mycobacterial cell or each of the target Mycobacterial species.

The nucleic acid may be analyzed by PCR using primers that anneal specifically to a signature nucleic acid sequence that occurs in the target Mycobacterial cell. The primers may anneal specifically to the signature nucleic acid sequence and/or may allow amplification of the specific signature nucleic acid. In some embodiments, the signature nucleic acid is 16S rRNA. In one embodiment, the signature nucleic acid sequence may be the insertion element IS900 for MAP and the nucleic acid sequence may be analyzed using a probe specific for IS900. In one embodiment, the signature nucleic acid sequence may be the insertion element IS1245 for MAH and the nucleic acid sequence may be analyzed using a probe specific for IS1245. In one embodiment, the signature nucleic acid sequence may be the f57 sequence for MAP, and the nucleic acid sequence may be analyzed using a probe specific for the f57 sequence. In one embodiment, the signature nucleic acid sequence may be the IS6110 sequence for MTB, M bovis and BCG, and the nucleic acid sequence may be analyzed using a probe specific for the IS6110 sequence. To increase the specificity more than one, more than two, more than three, more than four, more than five, more than six, more seven or more than eight signature sequences may be considered for each Mycobacteria to be detected. In one embodiment, at least 1, 2, 3, 4, 5, 6, 7, 8, 9, 10, 15, 20, 25, 30, 35, 40, 45, 50, 55, 60, 65, 70, 75, 80, 85, 90, 95, 100, or more than 100 signature species for at least one Mycobacteria are evaluated in a single assay. For example, in one embodiment, the assay may contain probes specific for each of IS900, IS1245, f57 and IS6110. In one embodiment, the assay may contain primers specific for amplification of each of IS900, IS1245, f57 and IS6110. Exemplary assays that can be used to evaluate multiple signature sequences, include, but are not limited to, microarrays, and q-PCR.

The nucleic acid sequence may be analyzed by sequencing at least a portion of the genomic DNA or RNA. Methods for performing whole or partial genome sequencing are known in the art and include, but are not limited to, exome sequencing, whole genome sequencing, and 16S rRNA sequencing. In various embodiments, sequencing may be done through Sanger sequencing, or through high-throughput next-generation sequencing techniques (e.g., using an Illumina based Hi-Seq, or Mi-Seq or Life Technologies PGM based sequencing platform.)

Kits

The present invention also pertains to kits useful in the methods of the invention. Such kits comprise various combinations of components useful in any of the methods described elsewhere herein. For example, in one embodiment, the kit comprises components useful for performing mycobacterium phage assays as described herein. In one embodiment, the kit comprises D29 bacteriophage and at least one nucleic acid probe for detection of Mycobacteria. In one embodiment, the kit comprises at least one of IS900, IS1245, f57 and IS6110. In one embodiment, the kit contains additional components. In one embodiment, an additional component includes but is not limited to instructional material. In one embodiment, instructional material for use with a kit of the invention may be provided electronically.

Methods of Use

The assays of this invention are useful for bacteriophage quantitation in a variety of testing regimes. In addition to the use of the assay of this invention in molecular biological techniques and these assays can be used as semiquantitative assays for discriminating between diseased and asymptomatic subjects, assessing Crohn's disease (CD) severity, identifying latent paratuberculosis, as a guide to therapy in humans and to correlate treatment outcomes.

In one embodiment, the method of discriminating between diseased and asymptomatic subjects comprises performing the mycobacterium phage-based assay on a sample from a subject, calculating the number of infectious mycobacterium present in the subject based on the number of plaques detected in the mycobacterium phage-based assay, and identifying the subject as either diseased or asymptomatic based on the quantification of infectious mycobacterium present in the subject. In one embodiment, the subject is identified as diseased based on a calculation that the number of infectious mycobacterium present in the subject is increased by at least 2%, 3%, 4%, 5%, 6%, 7%, 8%, 9%, 10%, 20%, 30%, 40%, 50%, 75%, 100%, or greater than 100% compared to a comparator control value. Non-limiting examples of comparators include, but are not limited to, a negative control, a positive control, standard control, standard value, an expected normal background value of the subject, a historical normal background value of the subject, a reference standard, a reference level, an expected normal background value of a population that the subject is a member of, or a historical normal background value of a population that the subject is a member of. In one embodiment, the comparator is a level of infectious mycobacterium present in a sample obtained from a subject who is asymptomatic for a disease or disorder associated with mycobacterium infection.

In one embodiment, the method of assessing CD severity comprises performing the mycobacterium phage-based assay on a sample from a subject, calculating the number of infectious mycobacterium present in the subject based on the number of plaques detected in the mycobacterium phage-based assay, and identifying the subject as having, or at risk of developing, mild or severe CD based on the quantification of infectious mycobacterium present in the subject. In one embodiment, the subject is identified as having, or at risk of developing, severe CD based on a comparison of the number of infectious mycobacterium present in the subject to a comparator control value. Non-limiting examples of comparators include, but are not limited to, a negative control, a positive control, standard control, standard value, an expected normal background value of the subject, a historical normal background value of the subject, a reference standard, a reference level, an expected normal background value of a population that the subject is a member of, or a historical normal background value of a population that the subject is a member of. In one embodiment, the comparator is a reference level of infectious mycobacterium present in at least one subject having severe CD.

In one embodiment, the method of the invention allows detection of mycobacterium at very early stages of infection, and before any clinical symptoms are visible. The method allows identification of the presence of live mycobacterium when they are present in a sample at very low numbers, for example less than 10 cells per sample.

In one embodiment, the method of the invention is used to monitor the efficacy of a treatment, and to screen for whether the numbers of bacteria are reducing as treatment is given.

Pharmaceutical Compositions and Formulations

The invention also encompasses the use of pharmaceutical compositions for inhibiting or disrupting microorganism growth or treating a microbial infection in a subject. Such a pharmaceutical composition may consist of an antibiotic composition in a form suitable for administration to a subject. Suitable agents used to treat Mycobacterial infections are well known in the art and include, but are not limited to, Isoniazid, Rifamycin, Pyrazinamide, Ethambutol, Para-amino salicylic acid, Streptomycin, Kanamycin, Ethionamide, Capreomycin, Cycloserine, Fluoroquinolones, Ciprofloxacin, Sparfloxacin, Ofloxacin, Dapsone, Clofazimine and Macrolides.

The antibiotic may be present in the pharmaceutical composition in the form of a physiologically acceptable salt, such as in combination with a physiologically acceptable cation, as is well known in the art.

In an embodiment, the pharmaceutical compositions useful for practicing the method of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for oral, rectal, vaginal, topical, transdermal, ophthalmic, intrathecal or another route of administration. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention or reduction of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; antiseptics; antiviral agents; anticoagulants; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, PA), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Administration/Dosing

In one embodiment, the invention relates to methods of treatment or prevention of a disease or disorder associated with a microbe identified using the phage-based assay of the invention. Administration of the therapeutic agent in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the subject, and whether prevention or treatment is to be achieved. Such factors can be readily determined by the clinician employing animal models or other test systems which are well known to the art.

The regimen of administration may affect what constitutes an effective amount. The therapeutic formulations may be administered to the patient either prior to or after the onset of pathogenic colonization, biofilm formation, and/or infection in a patient. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to prevent, reduce or disrupt pathogenic colonization, biofilm formation, and/or infection in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of breathing control disorders in a patient.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

In one embodiment, the present invention is directed to a packaged pharmaceutical composition comprising a container holding a therapeutically effective amount of a compound of the invention, alone or in combination with a second pharmaceutical agent; and instructions for using the compound to prevent or reduce the growth or proliferation of microorganisms or biofilm-embedded microorganisms on at least one surface of a medical device or a subject's body.

Routes of Administration

Routes of administration of any of the compositions of the invention include rectal, transdermal, transmucosal (e.g., sublingual, lingual, (trans)buccal, (trans)urethral, vaginal (e.g., trans- and perivaginally), (trans)rectal, intravesical, and topical administration.

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, gels, lotions, oil-in-water or water-in-oil emulsions such as creams, ointments or pastes, and solutions or suspensions. Topically administrable formulations may, for example, comprise from about 1% to about 10% (w/v) active ingredient in a solvent, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide (DMSO), and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

Method and System for Detection of MAP and Other Atypical Mycobacteria in Human Samples Using Phage Assay One of the greatest obstacles to understanding that infection by MAP causes CD and other "autoimmune" diseases has been the difficulty in consistently and rapidly detecting and/or culturing the organism from human samples. There are no MAP culture or antibody tests offered by any laboratory in the world. All of the work in this area has been conducted in research laboratories. MAP is very difficult to culture and the only blood culture method which has been published in the medical and scientific literature requires 6 months. This method does not yield colonies on solid media which could be used for antibiotic resistance testing and then lengthy culture process precludes meaningful antibiotic resistance data that would be clinically useful.

One of the limitations of offering this test is that the gastroenterologists have not accepted that this organism causes CD. In addition, it is a difficult mycobacterial infection to treat with currently available antibiotics. However, there is great interest in the CD community and many patients, who fail the conventional immunosuppressive therapies, will obtain this test and seek treatment from internal medicine and primary care physicians who learn about MAP.

Until recently, the gold standard of detection/culture of human samples for MAP is the method of Dr. Saleh Naser (Naser S A et al., 2004, Lancet, 364:1039-1044). This method requires up to six months of incubation and thus has never been adopted by clinical laboratories.

Recently, more rapid methods of detection and or culture of the organism in human samples have been developed. Samples from 201 human subjects have been collected for the large ongoing study, which was funded by the Human Paratuberculosis Foundation entitled, "A comparison of laboratory culture methods and antibody assays to assess the prevalence of infection by *Mycobacterium avium* subsp. *paratuberculosis* in the blood of patients with Crohn's disease and control subjects" (Example 3). The study compares the detection and/or culture recovery rates among 6 laboratories and between the CD subjects and the non CD controls. This study was also a blinded study.

In addition, a preliminary examination of the data, without knowledge of the disease status of the subjects, has revealed some interesting findings that have application to the use of this rapid assay in the human population. Application of the MAP phage detection method to the human population has shown that only 16% of the study population is without evidence of mycobacterial infection. Overall, 55% of the study population is positive for MAP, which was identified by an IS900 Taqman probe-based qPCR, which is specific for MAP. Because the study is blinded, the proportion of CD patients with positive tests or the proportion of non CD controls with positive tests is unknown. The remaining 29% of the study population are positive for as yet unidentified mycobacteria. Another laboratory is growing MAP colonies on solid media with a new rapid culture method and this material can used for organism identification by whole genome sequencing. This part of the study can used for validation of the MAP/phage assay.

The present invention provides, in part, a rapid detection method for viable MAP in human blood. This organism has been found in higher prevalence in CD patients than in healthy subjects. The test uses a bacteriophage, D29, that attacks the viable MAP cells, which are released from human white blood cells (WBCs). The patient MAP organisms released from the lysed WBCs are inoculated onto a medium containing *Mycobacterium smegmatis* organisms that support D29 growth. The infected *M. smegmatis* cells burst and the phages infect surrounding *M. smegmatis* cells leaving a zone of clearing called a plaque. The DNA from the center of the plaque contains the DNA from the MAP cell that infected the patient. This DNA is harvested and then tested against a Taqman qPCR probe for IS900, which is specific for MAP. The number of plaques in the phage culture correlates to the number of viable MAP cells in the host and is a semiquantitative measure of the burden of infection. When this test becomes widely available, physicians can test various therapies, which attempt to eradicate MAP and cure the associated CD. There are some (but not many) patients who have been reported in the medical literature that have experienced profound remission/cure for many years.

The MAP phage assay is a semi-quantitative method and the plaque count correlates to the number of viable MAP organisms in the subject sample. In the overall study, the plaque count ranged from none to as many as 700 plaques in some of the subjects.

In a related mycobacterial infection, leprosy, the bacterial burden correlates with the severity of the disease. For example, in the lepromatous form of the disease, there are innumerable organisms in the lesions and the disease is severe. It is highly probable that the subject with the plaque count of 700 is a CD patient and that this subject has a high Crohn's disease activity index (CDAI). The plaque count may be used in conjunction with the CDAI or may be incorporated into a modified form of the CDAI for an assessment of disease severity.

Another use of the plaque count assesses whether elimination of the viable MAP organism detected by the plaque assay and using an undetectable plaque count as the target leads to elimination of the underlying CD. This goal may be difficult or impossible to achieve using already available antibiotics. When latent tuberculosis infection is identified, subjects are treated to eradicate the latent tuberculosis infection. Similarly, the MAP phage assay are probably used to identify latent paratuberculosis infection and subjects who are asymptomatic, but infected by MAP, are treated for this infection. Ultimately, public health measures that reduce the burden of MAP in the environment can lead to lower rates of infection, and vaccines can be developed to prevent human infection from occurring in the first place. Veterinarians from around the world have already banded together in the past year to improve JD control.

Because a significant portion of the human population is infected and because many of these people are asymptomatic, the plaque count are likely correlated with the presence or absence of disease. The non CD controls can have a mean plaque count and the CD subjects can have a mean plaque count. These means could be used to discriminate between the two populations. If the organism cannot be entirely eradicated from the host, a goal of treatment for MAP bacteremia may be achieving the mean MAP phage plaque count of the non CD controls.

The MAP phage assay can be used to decide where public health measures should be directed. For example, improved MAP/JD control measures are already under active discussion in the international veterinary community. Additional mycobacteria identified in the human population by this study may become the target of new public health measures.

One of the discoveries of the current study is that 39% of the mycobacterial infections in the study population are not identified as MAP because the plaque samples are negative for the IS900 sequence. The initial identification of these samples has indicated that they are IS1245 positive, which is consistent with another atypical *mycobacterium, Mycobacterium avium* Hominissuis (MAH). At this point, *Mycobacterium smegmatis*, (part of the MAP phage assay) cannot be ruled out as the explanation for this group of phage positive samples. The confirmation of the identity of this population awaits a whole genome sequencing of culture isolates. This step was performed after the code was broken at the end of the study in March, 2019. Any species other than MAP in the human population found by this method in blood represents a new and important way to diagnose additional mycobacterial infections in human blood.

Moreover, blood samples from patients with active tuberculosis are gathered and the MAP phage method is applied to demonstrate *M. tuberculosis* in human blood. The resulting data can be used in support of claims of this method to diagnose tuberculosis infection (latent or active) from human blood. This method can be more specific and more sensitive than the current Quantiferon method used to detect latent tuberculosis infection.

This method was the first to demonstrate MAP in human blood. Prior to the invention, the presence of MAP in human blood was neither assured nor obvious (refer to the ACG guidelines). Further, the method of the invention allows recovery of organisms in a low bacterial burden human infection.

The methods of the invention were also the first to show that blood is a useful sample for demonstrating mycobacterial infection in humans. Prior to the invention, other assays were only available for human testing on sputum samples in active TB cases. This application is a much more limited and ultimately less useful application than the method of the invention which allows for detection of latent TB infection.

Example 2

Description of the Rapid Phage Assay, Applied to Human PBMC Samples

Peripheral blood mononuclear cells (PBMCs) are centrifuged (2,500×g for 15 min) and resuspended in 1 ml Middlebrook 7H9 broth supplemented with 10% OADC (both Difco) and 2 mM anhydrous CaCl2 (Sigma-Aldrich). Samples are incubated at room temperature for 15 min to permit lysis of the PBMCs, due to osmotic shock, and release of internalized MAP/mycobacterial cells, making them available for detection by the phage amplification assay or culture. At this point, the 1 ml test sample is transferred to a 0.37 oz (11 ml) polypropylene flip-top vial (CNLL500, Capitol Vial of Alabama Inc.). The phage assay then proceeds as follows: $10^8$ D29 mycobacteriophages (100 µl) are added to each 1 ml test sample to infect any MAP/mycobacterial cells present and samples are incubated at 37° C. After 2 hours, the extraneous seed phages are inactivated by treatment with virucide (10 mM ferrous ammonium sulphate, Sigma-Aldrich) for 10 min, before virucide action is terminated by dilution of sample with 5 ml 7H9/OADC/2 mM CaCl2 broth. Incubation of samples at 37° C. resumes until a total of 3.5 hours have elapsed since beginning of the test, at which point the entire sample is plated with 1 ml *Mycobacterium smegmatis* mc2 155 sensor cells ($10^8$ CFU/ml) and 5 ml molten Middlebrook 7H9 agar (cooled to 55° C.) in Petri dishes. Once solidified, agar plates are incubated overnight at 37° C. and examined next day for evidence of zones of clearing ('plaques'), the presence of which would be indicative of the viable mycobacteria in the sample since only viable MAP/mycobacterial cells will support phage amplification and subsequent lysis to release D29 phages within the agar.

In order to confirm the identity of the *Mycobacterium* sp. that had given rise to the plaques in a sample, up to 10 plaques per sample are collected from plaque positive agar plates. DNA is extracted from the plaques using a Zymoclean gel DNA recovery kit (Zymo Research Corp.) and an IS900 Taqman probe-based qPCR method (Sidoti et al. 2011, Can. J. Microbiol. 57: 347-354) is carried out to confirm the presence or absence of MAP DNA. A PBMC sample is declared MAP positive if plaques are confirmed to contain MAP DNA, 'MAP negative' if no plaques are obtained, and 'inconclusive result' if plaques are obtained but plaque IS900 PCR does not yield a positive result. An 'inconclusive' result may indicate absence of MAP and hence potential presence of another *Mycobacterium* species, or it may simply be that the amount of MAP DNA recovered from the plaques is below the limit of detection of the plaque PCR.

Example 3

A Comparison of Laboratory Culture Methods and Antibody Assays to Assess the Prevalence of Infection by MAP in the Blood of Patients with CD and Control Subjects CD, a chronic disease affecting the gastrointestinal tract, is considered a dysregulated immune response to intestinal dysbiosis. MAP has been postulated to play a role in the development of CD. In livestock, especially cattle, MAP is the causative factor for a diarrheal disease called JD. MAP infection occurs at a higher prevalence in patients with CD compared to healthy controls (Feller M et al., 2007, Lancet. Infect. Dis., 7:607-613; Abubakar I et al., 2008, Inflamm. Bowel Dis., 14:401-410), but the current blood culture methods have required three to six months for growth of the organism and the current method is of relatively low reproducibility (Naser S A et al., 2004, Lancet, 364:1039-1044; Naser S A et al., 2009, Open Inf. J., 2:22-23).

The primary goals of this study are to demonstrate that many humans have bacteremia with viable MAP organisms, to definitively identify the cultured organisms and to confirm that CD patients have a significantly higher rate of MAP infection than individuals that do not have CD. It was also investigated whether other mycobacteria besides MAP and MAH cause bacteremia and whether the infection is persistent or transient. A secondary goal is to compare more recent rapid culture methods from three laboratories and MAP antibody studies from several laboratories.

Blood cultures and serologic tests for MAP were performed on whole blood samples obtained from 201 subjects. The study subjects included 70 patients with CD (60) or ulcerative colitis (UC) (10) and 131 non-CD and non-UC controls. In a blind study, Buffy coats were cultured for MAP in three different laboratories and plasma was tested for MAP antibodies in three laboratories. The identity of the viable organisms that were cultured from the blood samples of the subjects can be established by whole genome sequencing.

Viable MAP bacteremia was found in a large number of the study subjects including many non-CD controls. Using the Grant phage assay (Grant et al., 2017, J Dairy Sci, 100(12):9723-9735), 113/201 (56%) of subjects were identified as having viable MAP bacteremia. Using the Bull culture method (Bull et al., 2017, Front Microbiol, 7:2112), 64/201 (32%) of subjects were identified as having viable MAP bacteremia. Using the Naser culture method (Naser S A et al., 2004, Lancet, 364:1039-1044; Naser S A et al., 2009, Open Inf. J., 2:22-23), 36/201 (18%) of subjects were identified as having viable MAP bacteremia. The best discriminators for CD were the Naser culture and the Zhang antibody methods (Zhang et al., 2017, bioRxiv: doi.org/10.1101/116574). Nine subjects who had a positive MAP/phage test initially also had a positive MAP/phage assay one year later.

Study Design and Participants

The first 159 subjects in the study were recruited from the practice of a gastroenterologist in Winter Park, Florida. In addition, 42 of the subjects were recruited from the Human Paratuberculosis Foundation website (humanpara.org) and the phlebotomy of the second group was performed at a site in New York City. Blood samples for the MAP/phage assay were obtained from subjects 161, 162, 167, 170, 175, 177, 178, 180 and 182 in the summer of 2018 and then one year later in the summer of 2019. A second sample was obtained from the above subjects to determine if they had a persistent MAP infection.

Diagnosis and Diagnostic Categorization

Blood samples (35 mL) were collected from all participants at enrollment in EDTA blood collection tubes. Buffy coat specimens were prepared from the whole blood samples and then shipped by overnight courier to each of the laboratories performing the cultures. The plasma from the blood samples was collected and frozen until a later date of shipment to the laboratories performing serologic studies.

QFT-GIT and T-SPOT.TB were done and interpreted in real time at the Tuberculosis Research Centre (Imperial College London, London, UK) according to the manufacturer's instructions and as described by Whitworth and colleagues (Naser S A et al., 2004, Lancet, 364:1039-1044). The second-generation IGRA used the T-SPOT.TB platform and incorporated ESAT-6, CFP-10, and Rv3615c; the ESAT-6-free IGRA incorporated CFP-10, Rv3615c, and Rv3879c. The laboratory scientists were masked to all clinical information, diagnoses, and personal identifiers.

Statistical Analysis

The detection rates of the culture methods for viable MAP bacteremia in order of the highest to lowest rate are: 1) Grant phage assay (113/201 or 56%), 2) Bull culture (64/201 or 32%), and 3) Naser culture (36/201 or 18%).

To investigate the independent relationships of the culture and the serologic methods or a combination of the culture and serologic methods with the presence of MAP and the clinical diagnosis in subjects (i.e., CD, UC and controls (non-CD or UC)), a logistic regression model was used for association analyses. The significant findings regarding associations with MAP culture and/or antibody data are provided using the odds ratio (OR) and its 95% confidence interval (CI) for having CD or having either CD or UC rather than a p-value. The OR data for all culture methods is presented adjusted for age and gender which is more robust, taking into account the potential age and gender influence, than the unadjusted odds ratio data which is also included.

The highest correlation to a MAP culture method occurred with the Naser culture method which had a significant p value of less than 0.05 for the CD patients in comparison to non-CD controls.

The associated p-value was 0.037 with an OR (95% CI) of 2.36 (1.06, 5.28) for the Naser culture method for MAP positivity corresponding to CD patients supports the predictive power of this culture method. This was also true when UC subjects were included along with the CD subjects in the analysis p-value=0.006 and OR (95% CI): 3.19 (1.40, 7.23).

The Bull culture method showed a significant OR for positive MAP cultures, but the Bull and Grant assays did not make the prediction model. However, the Bull and Grant methods detected a higher proportion of MAP infections in non-CD/UC controls.

Amongst the several serology tests, the highest correlation to the presence of CD occurred with the Zhang Hsp antibody. To define a cutoff value of the Zhang Hsp assay to predict a patient's diagnosis as CD, logistic regression was used to model the data, and the cutoff was chosen based on the value that provided the best classification rate. At a cutoff value >0.74, this method had the best ability to discriminate between CD patients and non-CD controls (OR (95% CI) of having CD comparing Zhang Hsp>0.74 vs. Zhang Hsp≤0.74: 2.40 (1.25, 4.61)) with p-value 0.009 and fisher exact p value 0.020. The Bach pknG antibody also had a significant correlation to the CD/UC patients as compared to the non-CD/UC controls.

Spearman correlation showed Zhang Hsp antibody assay had a weak (correlation=0.28, p=0.03) correlation with the HB index and the Grant Phage Plaque count showed a weak (correlation=0.12, p=0.37) (0.36) correlation with disease severity. It is worth noting that the range of the HBI in the study population was limited and few patients had an HBI greater than 5.

The combination of the Naser culture antibody and the Zhang Hsp Ab was the best discriminator between the CD patients and the non-CD controls for the study population.

The following caveat applies to all of the above observations. These statistics reflect a population which was not randomized for age, gender, disease severity, or health.

All of the 9 subjects, who had an initial positive MAP test and from whom a second sample was obtained one year later, were positive on the second MAP/phage assay.

The results of this study demonstrate that MAP infection is common in the human population with a high prevalence in patients with CD and UC but also in patients with other "autoimmune" diseases as well as in asymptomatic subjects. The herein described study also definitively identified the viable organisms recovered from the blood of the study subjects as MAP through WGS and comparison with MAP isolates in a large genome bank. Furthermore, a rapid (2 day) culture method that detects viable mycobacteria, including MAP, was demonstrated (Example 2). The study has also demonstrated that once established the infection is often persistent and that the host cannot eliminate the infection. Finally, it was shown that other mycobacterial species besides MAP infect the human host. Any assertion that MAP is not present in human tissue (Lichtenstein G R et al., 2018, Am. J. Gastroenterol., 113:481-517) should be abandoned in light of the findings of the 6 participating laboratories in this study.

The discovery of better therapies can be applied in controlled clinical trials that target and eliminate MAP. The mechanism of diarrhea caused by MAP (whether in cattle or humans) should be explained. MAP prevalence studies should be conducted in other, as yet unexplained "autoimmune" diseases, including type I diabetes mellitus, Sjogren's syndrome, systemic lupus erythematosus, asymmetric lateral sclerosis, systemic sclerosis, celiac disease, and the neurodegenerative diseases, including Alzheimer's disease and Parkinson's disease.

It was also found that a significant number of subjects without CD including some asymptomatic subjects have MAP bacteremia. This phenomenon resembles the infection in cattle in which only a minority of infected animals (about 10%) have advanced JD (Magombedze G et al., 2013, PLoS ONE, 8:e76636).

Finally, unless it can be proven that MAP does not cause disease in any human host, this organism should be regarded as at least a zoonotic pathogen that causes disease in humans. MAP has been cultured from human breast milk and thus is potentially a human pathogen (Naser S A et al., 2000, Am. J. Gastroenterol., 95:1094-1095). Public health measures for better control of JD should be enacted by governments worldwide.

Example 4

Whole Genome Sequencing of Bacterial Isolates

Figure 2:
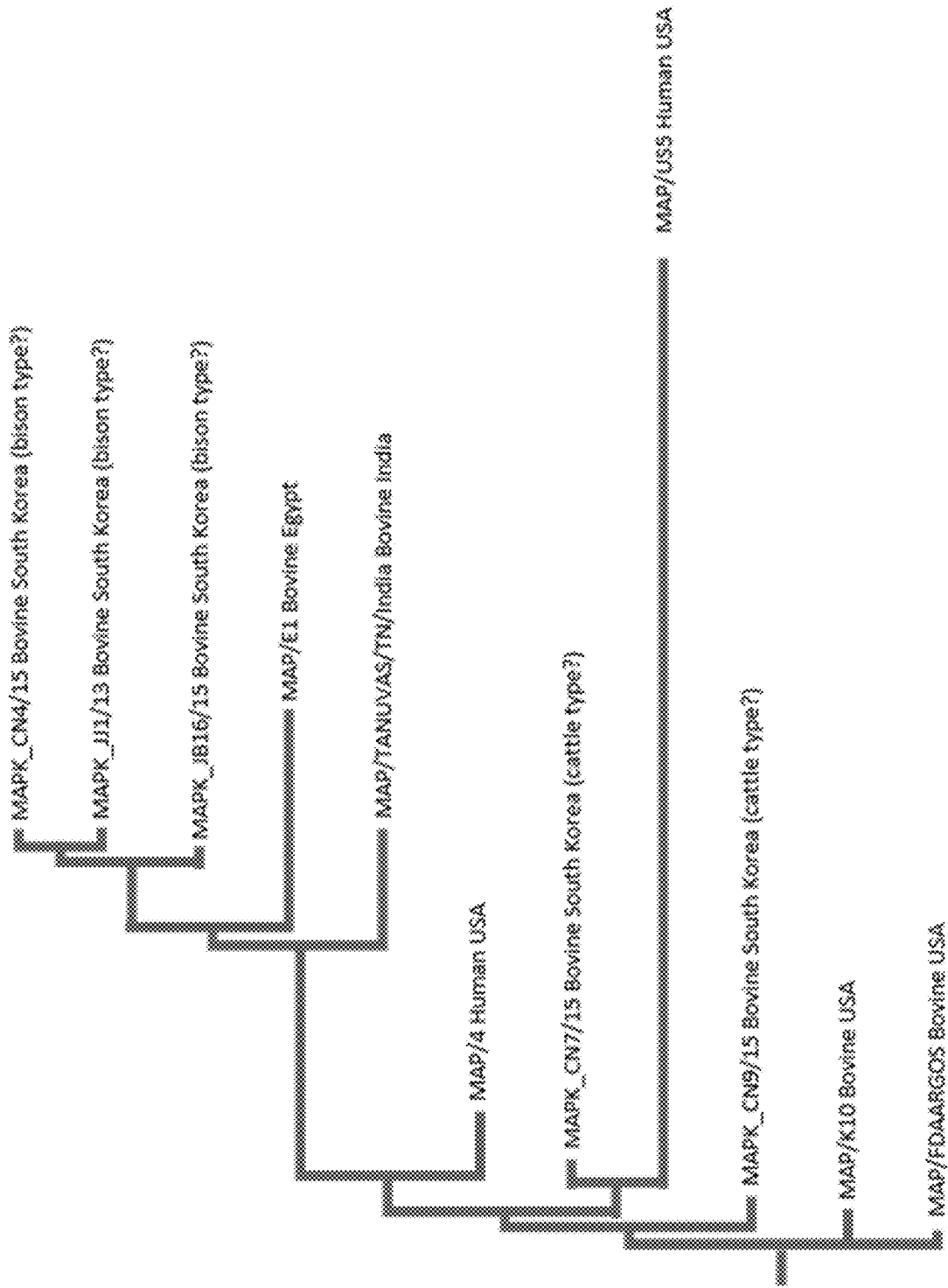
FIG. 2 depicts a phylogenetic tree of the relationship of the US5 strain identified in a patient sample to several complete assembled MAP genomes.

Whole genome sequencing (WGS) has been performed on a MAP culture isolate recovered from one subject who had a concurrent sample that was positive on the MAP/phage assay. The full genome sequence has been analysed for this particular strain and a phylogenetic tree of its relationship to several complete assembled MAP genomes is shown in FIG. 2. This strain (referred to as US5) clusters as a C-type relatively near the only other human strain to be assembled (MAP/4) in this thread. This isolate has unique insertions and deletions (INDELs) that include 233 single nucleotide polymorphisms (SNPs) plus 26 insertions and 12 deletions compared with MAP4 and 170 SNPs plus 13 insertions and 54 deletions compared with MAPK10. Some of these SNPs are interesting in that they predict some significant peptide alterations that are found in both MAP4 and US5 but not MAPK10.

Additional WGS data on 40 samples from multiple other subjects is also being obtained.

Types of mycobacteria, in addition to MAP, that have been recovered from recent non-conventional culture methods of human samples include, *M avium* complex (MAC), *M avium* hominissuis (MAH), *M tuberculosis* (MTB), *M bovis, M silvaticum* and BCG from human blood samples.

The host range of D29, the phage used in the MAP/phage assay, includes *M smegmatis, M avium, M bovis*, MTB, *M scrofulaceum* and *M ulcerans*. PCR probes specific for these organisms could be used in conjunction with the phage assay to identify these organisms.

Based on the preceding work involving recovery of mycobacteria from recent non-conventional culture methods, the MAP/phage assay for commercial use will include PCR probes such as IS6110 to identify plaque positive samples that are negative for the IS900 sequence and f57 sequence that identify MAP. The IS6110 sequence is positive in MTB, *M bovis* and BCG. The addition of these other probes will allow for identification of most (but not necessarily all) of the mycobacteria that are found on the MAP/phage assay.

Nine subjects in the MAP/CD study showed repeat positivity on MAP/phage assays that were obtained one year apart. This finding demonstrates that for many subjects, their MAP infection is persistent and cannot be cleared by the host. From these 9 subjects, DNA recovered from the plaques was positive with the IS900 PCR probe. This DNA was then confirmed using an f57 PCR probe. The inclusion of an F57 probe may increase the sensitivity and specificity of the assay.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A method of treating Crohn's Disease in a subject in need thereof comprising the steps of:
  a) obtaining a human blood or peripheral blood mononuclear cell (PBMC) sample from a subject diagnosed with Crohn's Disease;
  b) lysing cells of the sample to release any viable target mycobacterial cell;
  c) admixing a broad host range mycobacteriophage with the sample under conditions suitable to allow the bacteriophage to infect any viable target mycobacterial cell present in the sample;

d) removing any bacteriophage not infecting a viable target mycobacterial cell;
e) admixing at least a portion of the admixture of step c) following the removal of step d) with bacteria capable of supporting replication of the bacteriophage;
f) plating at least a portion of the admixture of step e) on a substrate to support growth of the bacteria;
g) quantifying the number of bacteriophage plaques that form;
h) discriminating between infected and asymptomatic subjects, comprising identifying the subject as infected when the number of bacteriophage plaques is statistically significantly greater than a reference number of bacteriophage plaques, or as asymptomatic when the number of bacteriophage plaques is not statistically significantly greater than a reference number of bacteriophage plaques, wherein the reference number of bacteriophage plaques is a reference number of plaques in asymptomatic human hosts; and
i) administering a pharmaceutical composition for inhibiting or disrupting microorganism growth or treating a microbial infection to a subject identified as infected.

2. The method of claim 1, wherein the cells are lysed by osmotic shock.

3. The method of claim 1, wherein the sample is from a human suspected of being infected with the target mycobacterial cell.

4. The method of claim 3, wherein the target mycobacterial cell is selected from the group consisting of *Mycobacterium avium* subspecies *paratuberculosis* (MAP), *Mycobacterium avium* complex (MAC), *Mycobacterium avium* hominissuis (MAH), *Mycobacterium tuberculosis* (MTB), *Mycobacterium leprae, Mycobacterium vaccae, Mycobacterium celatum, Mycobacterium kansasii, Mycobacterium gordonae, Mycobacterium porcinum, Mycobacterium cheloni, Mycobacterium flavescens, Mycobacterium bovis, Mycobacterium sylvaticum* and *Mycobacterium bovis Bacillus* Calmette Guerin (BCG).

5. The method of claim 1 wherein the bacteriophage is D29 or TM4.

6. The method of claim 1 further comprising the step of analyzing DNA from a lysed target mycobacterial cell obtained from a bacteriophage plaque to identify a signature DNA sequence that occurs in the target mycobacterial cell.

7. The method of claim 6 wherein the DNA is analyzed by a method selected from the group consisting of whole genome sequencing (WGS) and a PCR based DNA amplification system.

8. The method of claim 6 wherein the DNA is analyzed by PCR using primers that anneal specifically to a signature DNA sequence that occurs in the target mycobacterial cell.

9. The method of claim 8, wherein the signature DNA sequence is selected from the group consisting of IS900, IS1245, f57 and IS6110.

10. The method of claim 1, further comprising a step of identifying latent paratuberculosis in asymptomatic humans.

\* \* \* \* \*